(12) United States Patent
Erdogan

(10) Patent No.: US 8,517,966 B2
(45) Date of Patent: Aug. 27, 2013

(54) SCREW NAIL CORRECTING APPARATUS

(76) Inventor: Fatma Gulru Erdogan, Ankara (TR)

( * ) Notice: Subject to any disclaimer, the term of this patent is extended or adjusted under 35 U.S.C. 154(b) by 44 days.

(21) Appl. No.: 13/141,143

(22) PCT Filed: Dec. 28, 2009

(86) PCT No.: PCT/TR2009/000163
§ 371 (c)(1),
(2), (4) Date: Jun. 21, 2011

(87) PCT Pub. No.: WO2010/077218
PCT Pub. Date: Jul. 8, 2010

(65) Prior Publication Data
US 2011/0257570 A1  Oct. 20, 2011

(30) Foreign Application Priority Data
Dec. 30, 2008  (TR) .............................. a 2008 09970

(51) Int. Cl.
| | | |
|---|---|---|
| A61F 5/00 | (2006.01) | |
| A61F 5/04 | (2006.01) | |
| A61F 2/46 | (2006.01) | |
| A61F 2/00 | (2006.01) | |
| A61B 17/56 | (2006.01) | |
| A61B 17/00 | (2006.01) | |
| A61B 17/58 | (2006.01) | |
| A61B 17/60 | (2006.01) | |

(52) U.S. Cl.
USPC ........ 602/31; 602/5; 602/23; 602/30; 606/53; 606/54; 606/55; 606/56; 606/57; 606/59; 606/86 R; 606/101

(58) Field of Classification Search
USPC ................ 602/30–31, 5, 23; 606/53–57, 59, 606/86 R, 101
See application file for complete search history.

(56) References Cited

U.S. PATENT DOCUMENTS

| | | | | |
|---|---|---|---|---|
| 884,376 | A | * | 4/1908 | Foster ............................. 602/31 |
| 1,708,716 | A | * | 4/1929 | Andersen ........................ 602/31 |
| 2,567,601 | A | * | 9/1951 | Heinold et al. ................. 602/31 |
| 2,746,451 | A | | 5/1956 | Parker |
| 3,032,032 | A | * | 5/1962 | Gifford .......................... 602/31 |
| 4,057,055 | A | * | 11/1977 | Clark ............................. 602/31 |
| 4,086,656 | A | * | 4/1978 | Brown ......................... 708/444 |
| 5,643,258 | A | * | 7/1997 | Robioneck et al. ............ 606/54 |
| 2009/0048551 | A1 | * | 2/2009 | Liberson ........................ 602/31 |
| 2010/0137771 | A1 | * | 6/2010 | Harada ........................... 602/31 |
| 2012/0238930 | A1 | * | 9/2012 | Yoshino et al. ................ 602/31 |

FOREIGN PATENT DOCUMENTS

| | | |
|---|---|---|
| DE | 10 2006 010299 A1 | 9/2007 |
| WO | 2007/102156 A2 | 9/2007 |

* cited by examiner

*Primary Examiner* — Patricia Bianco
*Assistant Examiner* — Brandon L Jackson
(74) *Attorney, Agent, or Firm* — Ziegler IP Law Group, LLC.

(57) ABSTRACT

A screw nail correcting apparatus used for treating ingrown nails seen in human feet and/or hands adapts to different nail widths and to the changes that may occur in time on the same nail and practically enables pulling of the nail with an amount of force complying with the requirement. The fact that the apparatus is not a single piece and that it can be mounted separately from both sides of the nail provides ease of use, and the screw mobile part in the middle thereof helps to adjust the tautness according to the requirement of the nail at the concerned moment.

11 Claims, 3 Drawing Sheets

SCREW NAIL CORRECTING APPARATUS

CROSS-REFERENCE TO RELATED APPLICATIONS

This application is the U.S. National Stage of International Application No. PCT/TR2009/000163, having an international filing date of Dec. 28, 2009, which designated the United States of America and which was published under PCT Article 21 (2) as Publication No. WO2010/077218 A1 on Jul. 8, 2010, and which claims priority to Turkish Application No. 2008/09970, filed Dec. 30, 2008, the disclosure of which is incorporated herein by reference in its entirety.

BACKGROUND

1. Field

The aspects of the disclosed embodiments relate to a screw nail correcting apparatus used for treating ingrown nails seen in human feet and/or hands.

2. Brief Description of Related Developments

Today it is known that studies have been conducted for years concerning this issue and that technically similar apparatuses are designed. These are apparatuses which are as long as the width of the nail, generally comprised of a single piece, and designed such that they grip the nail from both sides with their inwardly folded ends. In these apparatuses, it is mostly aimed to prevent ingrown nail and enable the nail to grow properly, by ensuring that the nail advances within the clasps when growing. While some of the current apparatuses provide for proper growth of the nail by guiding it, others enable the nail to be corrected by exerting physical power to the ingrown nail parts in the opposite direction. Applying the apparatuses known in the art on nails with different widths is not practical. Besides, these apparatuses cannot provide a practical and easy-to-apply solution to the possible changes that might occur in time on the treated nail.

SUMMARY

One aspect of the disclosed embodiments relates to an apparatus for correcting the side(s) of the nail which grow digging into the flesh and for treating the ingrown nail, and it can be practically adjusted according to different nail widths and to the changes that may occur in time on the same nail. Thus, it will be possible to prevent the loosening that will occur in time as the nail is unfolded (straightened), and to pull the nail with the same force and tautness constantly. It is sufficient to turn the screw (3) on the apparatus to provide the tautness.

One aspect of the apparatus of the disclosed embodiments allows it to be joined after being applied separately to both sides of the nail, enabling this application to be carried out also by the patients, because the apparatus does not have a static structure. It is possible to exert a desired amount of force to the ingrown nail in the opposite direction since it can be narrowed and enlarged according to the nail width.

In accordance with aspects of the disclosed embodiments, the apparatus consists of two or more ratchet clasps (7); which are of great convenience especially for problematic and asymmetric nails but which can also be affixed to all nails separately on the sides of the nails such that they provide convenience in application, which are not single-piece and can be attached onto the end of the opposite ratchet clasp from 5 the desired point according to the width of the nail by the notches or round holes on its middle part; and elastic/semi-elastic band (6); and the screw adjustment billet (1) is connected to the ratchet clasps (7) from two sides. This provides convenience in connecting the screw adjustment billet (1) to the sides of the ratchet clasps (7) and thus for it to remain on the nail without slipping. Moreover, if desired, a bolster (12) can also be applied to allow the apparatus to remain on the nail surface without slipping.

BRIEF DESCRIPTION OF THE DRAWINGS

The aspects of the disclosed embodiments will be described by way of example with reference to the appended drawings, in which.

DETAILED DESCRIPTION OF THE DISCLOSED EMBODIMENTS

Figure 1:
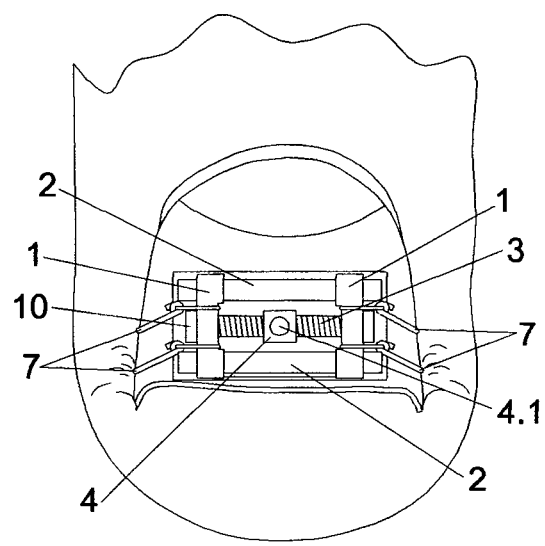
FIG. 1 is the top view of the apparatus in accordance with aspects of the disclosed embodiments affixed to the nail.
Figure 2:
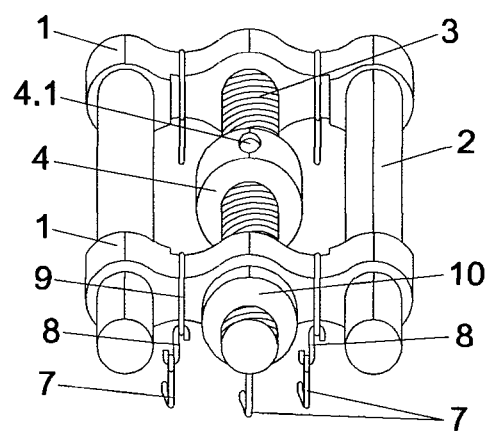
FIG. 2 is the top side perspective view of the apparatus.
Figure 3:
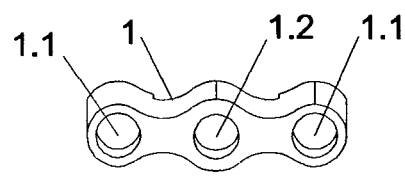
FIG. 3 is the side perspective view of the adjustment billet.
Figure 4:
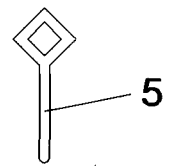
FIG. 4 is the view of the key.

The pieces/parts related to the apparatus in accordance with aspects of the disclosed embodiments are numbered as follows:

1. Adjustment billet
1.1. Pin hole
1.2. Screw socket
2. Pin
3. Screw
4. Adjustment nut
4.1. Key hole
5. Key
6. Elastic/semi-elastic band
6.1. Ratchet hole
7. Ratchet clasp
7.1 Lower ring
8. Additional clasp
9. Ring
10. Nut
11. Supporting apparatus
12. Bolster
13. Handle
14. Clasp holder
15. Clasp In one embodiment, an apparatus is comprised of adjustment billets (1); pins (2) and/or screws (3), an adjustment nut (4) and a key (5) that enable screws to be turned; a ring, hook, rubber or similar elastic materials or spirals that enable connection of this upper mobile part with the fixed lower part; elastic and/or semi-elastic materials (6) such as rubber, silicone or spring to establish the contact of the apparatus with the nail and ratchet clasps (7) coupled to the ends of them; additional clasps (8) or rings (9) that establish contact of them with the mobile screw part; nuts (10) in which the screw part can easily turn, narrow or enlarge; supporting apparatuses (11) that can be placed under the nail; and a bolster (12) which is placed in between the nail and the apparatus to prevent the apparatus from slipping away from the nail surface.

Figure 7:
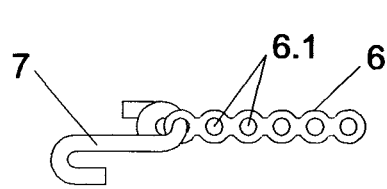
FIG. 7 is the view of the elastic/semi-elastic band affixed to the ratchet clasp.
Figure 8:
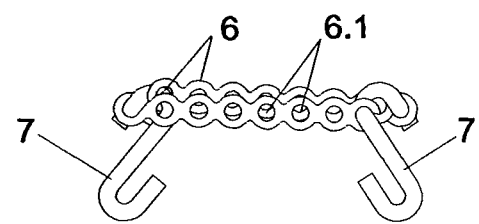
FIG. 8 is the view of the ratchet clasps coupled with the elastic/semi-elastic bands correspondingly.
Figure 9:
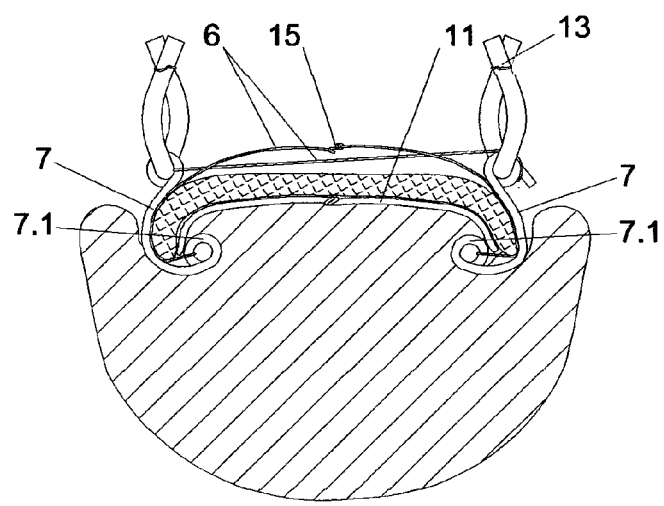
FIG. 9 is the front side view of the apparatus affixed to the nail from the lower ring.
Figure 10:
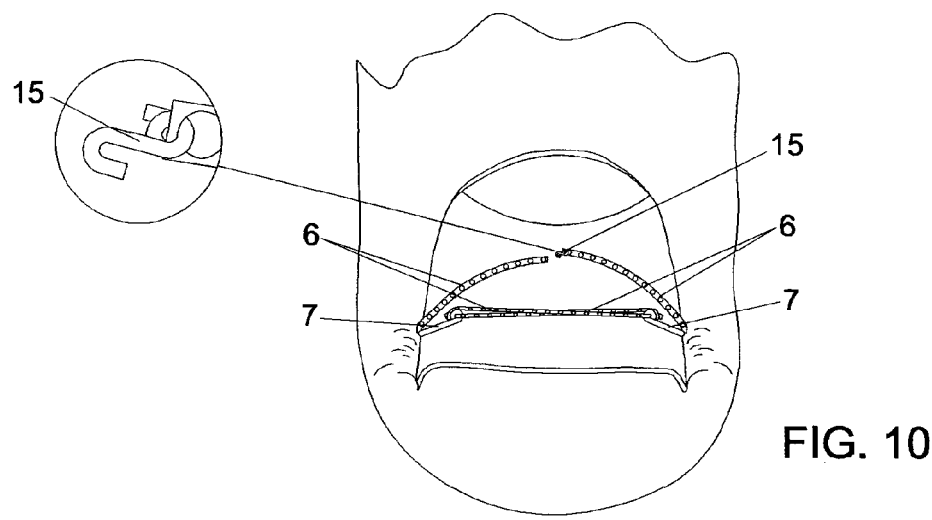
FIG. 10 is the top view of the ratchet clasps coupled with the bands coming from the lower and upper rings thereof.
Figure 11:
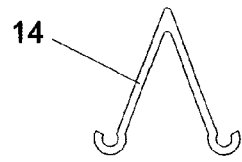
FIG. 11 is the view of the clasp holder.

The contact of the apparatus with the nail is provided by at least two or more opposing ratchet clasps (7) that can be engaged under the nail from both sides. Ratchet clasps (7) may be formed in shapes like "U" or "S" in order to be engaged to the sides of the nail. One end of the ratchet clasps (7) is produced in a form folded in the shape of a circle ending in a ratchet form in order for the additional clasps (8) to engage thereto and for the elastic/semi-elastic bands (6) having circular holes (6.1) thereon to be attached and not to get detached. (FIG. 7)

The additional clasps (8) can hold the ratchet clasp (7) on one side, while holding the ring (9) at the side of the adjustment billet (1) on the other side.

With the help of the holes (6.1) provided on them, elastic/semi-elastic bands (6) can be easily engaged to the ratchet parts of the clasps (7) with the desired width. These elastic/semi-elastic bands (6) that are independently attached from both sides enable a practical application suitable to apply to nails with all widths. Additionally, the ratchets at the end of the clasps (7) ease the application of elastic/semi-elastic bands (6) and allow the tautness to be adjusted as desired. The notch or the circular holes (6.1) on the elastic/semi-elastic band (6) provides the apparatus the feature of being applicable on nails with various widths just like a belt buckle.

Figure 5:
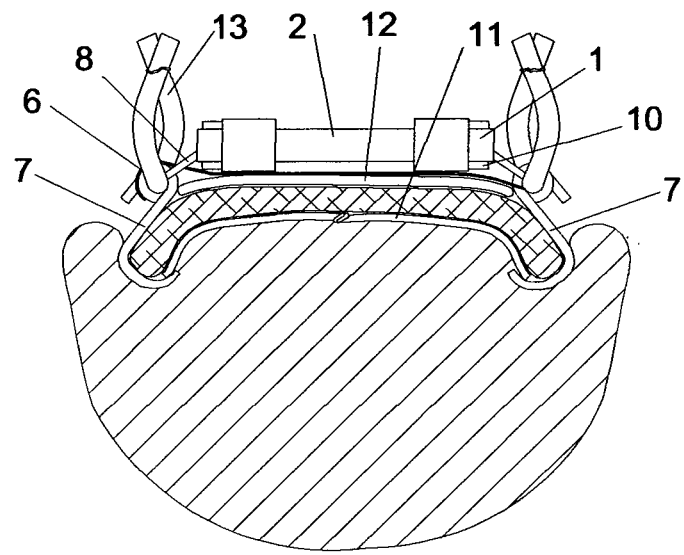
FIG. 5 is the front side view of the apparatus affixed to the nail.

Upon connection of the ratchet clasps (7) and the elastic/semi-elastic bands (6) that are coupled thereto by engagement through the clasps, the nail is gripped as desired and it helps the mobile part consisting of the pin (2), screw (3) and adjustment billet (1) that will be incorporated thereon, to remain still on the nail without slipping (FIG. 5). Increasing or reducing tautness of the clasps by moving the adjustment billets (1), which are provided on the mobile part that can be incorporated to this system, towards or away from each other, is provided by turning the screw (3). As this screw mobile part may be narrowed and loosened from both sides, it can also be narrowed and enlarged from a single side.

Figure 6:
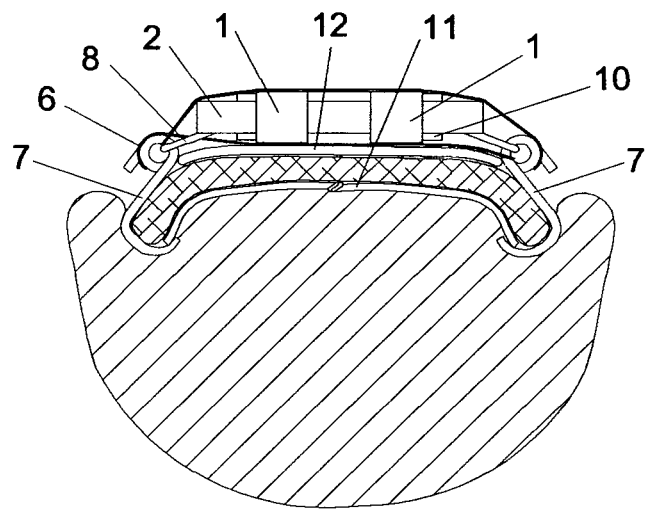
FIG. 6 is the front side view of the apparatus affixed to the nail (narrowed version)

In an alternative embodiment, the mobile part in the middle is first attached to one of the clasps (7). Then, the other clasp (7) is applied to the other nail side, and the mobile part in the middle is winded by elastic bands (6) the first of which passes from below while the second passes from above, helping the mobile part to remain still. (FIG. 6) Upon rotation of an adjustment nut (4), which is mountable to the middle or sides of the screw(s) (3) and on which a plurality of holes are notched, around its own axis by means of a suitable key (5) corresponding to the key holes (4.1), the screw(s) (3) are rotated around their own axes and the adjustment billets (1) are enabled to move towards (approach) and away from each other by moving forwards and backwards along the pins (2), thus the tautness applied 5 to the clasps (7) can be decreased or increased.

Even though increasing and decreasing the tautness of the ratchet clasps (7) which are coupled to the screw(s) (3) separately from both sides is important, the elastic/semi-elastic bands (6), which are coupled to the ends of the ratchet clasps and in the middle of which there are holes (6.1), and silicone or similar bolsters, which are placed or adhered at the bottom of the mobile screw part, and which prevent slipping on the surface of the nail, can also enable the screw (3) to remain still on the nail without slipping.

Rings (9), or additional clasps (8) or elastic/semi-elastic bands (6) or elastic/semielastic spirals are attached to provide connection directly on the screw (3) and/or to the edges of the adjustment billets (1) in order to provide the tautness between the ratchet clasps (7) and the screw(s) (3), and they enable the ratchet clasps (7) which grip the nail from a single or multiple regions to be drawn taut with a higher force as the screw (3) in the middle is narrowed and to try to unfold the nail.

When necessary (for folded nails), with the help of a supporting apparatus (11) to be placed under the nail, the nail is aimed to be loosened by the movement of the screw(s) (3) and by the clutch of ratchet clasps (7). The supporting apparatuses (11) that can be placed under the nail can be integral or used independently and they will help to unfold the folds of the nail edges by their features of enlarging and narrowing.

One or more pin holes (1.1) and/or screw sockets (1.2) are formed on the adjustment billets (1). While the elastic/semi-elastic bands (6) can be mounted to the screw(s) (3) by nuts (10), they can also be applied in different ways, such as to the edges of the adjustment billets whereby they establish connection of the clasps (7) with the apparatus and prevent the apparatus from slipping. Moreover, preventing the apparatus from slipping from the nail surface can also be ensured by placing a bolster (12) made of an elastic or non-elastic material between the nail and the apparatus.

While, in one embodiment, the apparatus can first be mounted on the nail as coupled to one of the ratchet clasps (7) and then completely mounted by the help of the other ratchet clasp (7), it can also be incorporated to the clasps (7) after the ratchet clasps (7) are mounted to the nail and connected to each other.

An additional second ring (7.1) is formed on the lower part of the ratchet clasp (7) for applying the inventive apparatus to severely inwardly curved nails. By means of the said ring (7.1), it will be possible to grip the extremely inwardly curved side of the nail from an inner curve. This way, the force applied on the nail sides will be able to be increased.

A second elastic/semi-elastic band (6) will be affixed to the second ring (7.1) provided on the lower part of the ratchet clasp (7), and the said band will be engaged to the ratchet part at the end of the ratchet clasp (7) of the opposing side via one of the holes (6.1) thereon. The elastic/semi-elastic band (6) extending from the upper ring of the ratchet clasp (7) can be affixed to the ratchet part at the end of the opposing ratchet clasp (7). That is to say, two elastic/semi-elastic bands (6) extending from the upper and lower rings of the ratchet clasp (7) can be engaged to the ratchet part of the ratchet clasp (7) of the opposing side.

In patients with thick walled nail sides, if the ratchet part of the ratchet clasp (7) disturbs the skin part next to it, as an alternative coupling form, a new clasp (15) can be incorporated to the free end (the end which is not coupled to the ratchet clasp) of the holed elastic-semi elastic bands (6) and the said new clasp (15) will be affixed to one of the holes (6.1) provided on the elastic-semi elastic bands (6) extending from the opposing side.

The clasp holder (14) facilitates affixing the new clasp (15), which is mounted to the other end of the band (6) that is not coupled to the ratchet clasp (7), to the holes (6.1) provided on the band (6) coming from the opposing side.

A handle (13) is provided attached to the upper ring of the ratchet clasp (7) to facilitate affixing the apparatus to the nail and to ensure that even a person who is not a professional and will use the apparatus can easily apply it. The handle (13) is a disposable piece, which is attached to the apparatus from its circular parts to facilitate affixing the apparatus as it may be difficult to hold and affix the apparatus directly by hand, and which enables the apparatus to be gripped by hand and can be disposed by cutting or opening its upper part after the apparatus is conveniently affixed.

The above description provides non-limiting examples of certain exemplary embodiments of the invention. However, it is apparent to persons skilled in the art that the invention is not limited to the details presented; rather, the aspects of the disclosed embodiments may also be implemented in other equivalent ways. The above description, as such, should be regarded as a descriptive presentation of the principles of the invention and not as limiting the invention. Therefore, the scope of the invention is only limited by the appended claims.

What is claimed is:

1. A nail correcting apparatus, which is used for treating ingrown nails seen in human feet or hands, and which can be adjusted according to different nail widths and changes that can occur in time on the same nail comprising:
    pins enabling connection of adjustment billets;
    the adjustment billets with pinholes and screw sockets in them, wherein the adjustment billets can move forward and backward on the pins, so as to move towards or away from each other;
    a screw threaded through the screw sockets, which can be twisted on its axis, enabling the adjustment billets to move towards or away from each other;
    an adjustment nut with key holes mounted on the screw, enabling the screw to be twisted around its own axis;
    a key positionable within the key holes on the adjustment nut, enabling the adjustment nut to be twisted leading to the screw's movements;
    ratchet clasps, connected to the screw on both sides, with enable bands to be tightened an not easily detached;
    the bands have ratchet holes on them that can be applied in an adjustable fashion, through ratchet parts to the ratchet clasps from both sides;
    rings that can be applied directly on the screw or to the adjustment billets, connecting the ratchet clasps to the screw in a tight manner;
    additional clasps which further connect the ratchet clasps with the screw so the screw does not slip or move;
    nuts which may enable the bands to be connect to the screw by means of contralateral ratchet holes, when required;
    a supporting apparatus placed under the nail to loosen inward nail curves by tightening and expanding as required; and
    a bolster placed between the nail and the adjustment billets helping the apparatus to be kept in place without slipping.

2. The apparatus according to claim 1, wherein the key holes are notched around the adjustment nut.

3. The apparatus according to claim 1, wherein the key enables the adjustment nut to be rotated around its axis and corresponds to the key holes.

4. The apparatus according to claim 1, wherein the band is assembled to the ratchets of the clasps in a desired width.

5. The apparatus according to claim 1, wherein the ratchet clasp comprises one end folded in a shape of a circle ending in a ratcheted form in order for the additional clasps to engage thereto and for the bands to be attached and not to get detached.

6. The apparatus according to claim 1, further comprising a second ring formed on a lower part of the ratchet clasp in order for the apparatus to be applied to severely inwardly curved nails.

7. The apparatus according to claim 1, wherein the ring is mounted on edges of the adjustment billets to provide tautness between the ratchet clasps and the screw.

8. The apparatus according to claim 1, wherein the bolster is comprised of elastic or non-elastic materials.

9. The apparatus according to claim 1, further comprising a handle, which is attached to an upper ring of the ratchet clasp and which is formed by joining and connecting its ends to facilitate affixing the apparatus to the nail.

10. The apparatus according to claim 1, further comprising a clasp which can be incorporated to a free end of the bands and can be affixed to one of the holes provided on the bands extending from an opposing side.

11. The apparatus according to claim 1, further comprising a clasp holder which facilitates affixing a clasp mounted to an of the band not coupled to the ratchet clasp to the holes provided on the band coming from an opposing side.

* * * * *